United States Patent [19]

Soldin

[11] Patent Number: 5,525,523
[45] Date of Patent: Jun. 11, 1996

[54] BINDING METHOD FOR FK-506- AND RAPAMYCIN-LIKE DRUGS WITH A NOVEL IMMUNOPHILIN

[75] Inventor: Steven J. Soldin, Washington, D.C.

[73] Assignee: Children's Research Institute, Washington, D.C.

[21] Appl. No.: 282,330

[22] Filed: Jul. 29, 1994

Related U.S. Application Data

[62] Division of Ser. No. 50,576, Apr. 21, 1993, Pat. No. 5,354,845.

[51] Int. Cl.$^6$ .................... G01N 33/538; G01N 33/545
[52] U.S. Cl. .................... 436/503; 436/504; 436/531; 436/541; 436/542; 436/815
[58] Field of Search .................... 436/501, 503, 436/531, 815, 541, 542, 504

[56] References Cited

U.S. PATENT DOCUMENTS

| | | | |
|---|---|---|---|
| 5,047,512 | 9/1991 | Handschumacher et al. | 530/402 |
| 5,109,112 | 4/1992 | Siekierka et al. | 530/350 |
| 5,196,352 | 3/1993 | Siekierka et al. | 436/501 |
| 5,362,629 | 11/1994 | Screiber et al. | 435/7.92 |

FOREIGN PATENT DOCUMENTS 9104321  4/1991  WIPO.

OTHER PUBLICATIONS

Siekierka, John et al., "A Cytosolic Binding Protein for the Immunosuppressant FK506 . . . ", Nature, vol. 341, 1989, pp. 755–757.

Jin et al., "Molecular Cloning of a Membrane–Associated Human FK–506– and Rapamycin–Binding Protein, FKBP–13", PNAS USA, 88:6677–81 (1991).

Nielsen, J. B., et al., PNAS USA, 89:7471–75 (1992).

Jin et al., "Molecular Cloning of a 25–kDa High Affinity Rapamycin Binding Protein, FKBP25", J. Biol. Chem., 267:10942–945 (1992).

Galat, A., et al., "A Rapamycin–Selective 25–kDa Immunophilin", Biochemistry, 31:2427–2434 (1992).

Donnelly, J. G., et al., "Purification of a 50– to 58–kDa Immunophilin . . . ", Transplantation Proceedings., 23:2886–89 (1991).

Fretz, H., et al., "Rapamycin and FK506 Binding Proteins (Immunophilins)", J. Am. Chem. Soc., 113:1409–11 (1991).

Yem, A. W., et al., "The Hsp56 Component of Steroid Receptor . . . ", J. Biol. Chem., 267:2868–71 (1992).

Primary Examiner—Mary E. Ceperley
Attorney, Agent, or Firm—Foley & Lardner

[57] ABSTRACT

A new homogeneous cytosolic binding protein (FKBP-14.6 immunophilin) having a molecular weight of about 14.6 kDa (calculated from its amino acid composition), reversibly binds the immunosuppressive drugs FK-506, rapamycin or chemically related compounds, but not cyclosporine. The FKBP-14.6 protein has a pI of 6.5–7.5, and the (partial) N-terminal amino acid sequence: NH$_2$-Lys-Leu-Pro-Tyr-Glu-Leu-Lys-X-Asn-Val-Lys-Ala-Phe-X-X-Lys-Val- (where X is undefined), and partial internal amino acid sequences -Val-Leu-Asp-Thr-Ala-Tyr-Glu-Tyr-Gly-Ala-Glu-Ala-Leu-Glu-, -Glu-Phe-Thr-Pro-Val-Phe-Gln-Ala-X-Phe- and -Ser-Leu-Val-Pro-Leu-Val-Gly-X-Lys- (where X is undefined). This N-terminal amino acid sequence exhibits no homology to FKBP-12 or membrane-associated FKBP-13. THe FKBP-14.6 is isolated from the cytosol of mammalian tissues, preferably calf thymus, and can be used in diagnostic and purification procedures involving FK-506 and rapamycin-type immunosuppressant drugs.

11 Claims, 8 Drawing Sheets

SEQUENCE LISTING ( 1 ) GENERAL INFORMATION:

( i i i ) NUMBER OF SEQUENCES: 6

( 2 ) INFORMATION FOR SEQ ID NO:1:

( i ) SEQUENCE CHARACTERISTICS:
       ( A ) LENGTH: 17 amino acids
       ( B ) TYPE: amino acid
       ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:1:

Lys  Leu  Pro  Tyr  Glu  Leu  Lys  Xaa  Asn  Val  Lys  Ala  Phe  Xaa  Xaa  Lys
   1                   5                        10                       15

Val ( 2 ) INFORMATION FOR SEQ ID NO:2:

( i ) SEQUENCE CHARACTERISTICS:
       ( A ) LENGTH: 14 amino acids
       ( B ) TYPE: amino acid
       ( D ) TOPOLOGY: linear ( i i ) MOLECULE TYPE: peptide ( v ) FRAGMENT TYPE: internal ( x i ) SEQUENCE DESCRIPTION: SEQ ID NO:2:

Val  Leu  Asp  Thr  Ala  Tyr  Glu  Tyr  Gly  Ala  Glu  Ala  Leu  Glu
   1                   5                        10

( 2 ) INFORMATION FOR SEQ ID NO:3:

( i ) SEQUENCE CHARACTERISTICS:
       ( A ) LENGTH: 10 amino acids
       ( B ) TYPE: amino acid
       ( D ) TOPOLOGY: linear ( i i ) MOLECULE TYPE: peptide ( i i i ) HYPOTHETICAL: NO ( v ) FRAGMENT TYPE: internal ( x i ) SEQUENCE DESCRIPTION: SEQ ID NO:3:

Glu  Phe  Thr  Pro  Val  Phe  Gln  Ala  Xaa  Phe
   1                   5                        10

( 2 ) INFORMATION FOR SEQ ID NO:4:

( i ) SEQUENCE CHARACTERISTICS:
       ( A ) LENGTH: 9 amino acids
       ( B ) TYPE: amino acid
       ( D ) TOPOLOGY: linear (i i) MOLECULE TYPE: peptide (i i i) HYPOTHETICAL: NO (v) FRAGMENT TYPE: internal (x i) SEQUENCE DESCRIPTION: SEQ ID NO:4:

Ser Leu Val Pro Leu Val Gly Xaa Lys
1               5

(2) INFORMATION FOR SEQ ID NO:5:

(i) SEQUENCE CHARACTERISTICS:
  (A) LENGTH: 17 amino acids
  (B) TYPE: amino acid
  (D) TOPOLOGY: linear (i i) MOLECULE TYPE: peptide (i i i) HYPOTHETICAL: NO (v) FRAGMENT TYPE: N-terminal (x i) SEQUENCE DESCRIPTION: SEQ ID NO:5:

Gly Val Gln Val Phe Thr Ile Ser Pro Gly Asp Gly Asn Thr Phe Pro
1               5                   10                  15

Lys (2) INFORMATION FOR SEQ ID NO:6:

(i) SEQUENCE CHARACTERISTICS:
  (A) LENGTH: 17 amino acids
  (B) TYPE: amino acid
  (D) TOPOLOGY: linear (i i) MOLECULE TYPE: peptide (i i i) HYPOTHETICAL: NO (v) FRAGMENT TYPE: N-terminal (x i) SEQUENCE DESCRIPTION: SEQ ID NO:6:

Thr Gly Ala Glu Gly Lys Arg Lys Leu Gln Ile Gly Val Lys Lys Arg
1               5                   10                  15

Val

BINDING METHOD FOR FK-506- AND RAPAMYCIN-LIKE DRUGS WITH A NOVEL IMMUNOPHILIN

This application is a division of application Ser. No. 08/050,576, filed Apr. 21, 1993, now U.S. Pat. No. 5,354,845.

BACKGROUND OF THE INVENTION

1. Field of the Invention

The invention relates to the family of cytosolic immunosuppressant drug binding proteins termed immunophilins. More specifically, this invention relates to a novel immunophilin.

2. Background Information

Cyclosporine, FK-506 and rapamycin are drugs of clinical importance in suppressing organ transplant rejection by suppression of the immune system. Although the mechanism of action of these drugs is not yet understood, it is clear that an initial step in this mechanism consists of the high affinity binding of the drug to water-soluble cytoplasmic (cytosolic) binding proteins termed immunophilins.

Several immunophilins with various drug binding specificities have been identified. Certain of them have been purified to homogeneity, and completely or partially sequenced. At least five specific binding proteins for the macrolides FK-506 and rapamycin are known. The most abundant of these is the immunophilin termed FKBP-12, a protein of molecular mass of about 11–12 kDa that has been purified to homogeneity (Siekierka et al., U.S. Pat. No. 5,109,112; Schreiber et al., WO 91/04321; Lane et al., J. Prot. Chem., 10:151 (1991); Soldin, U.S. patent application Ser. No. 07/782,761).

A membrane-associated human FK-506 and rapamycin binding protein of molecular mass of about 13 kDa and termed FKBP-13 has been cloned from a human carcinoma cDNA library and sequenced; it has a 51% nucleotide sequence identity and 43% amino acid sequence identity to FKBP-12 and, like FKBP-12, exhibits rotamase activity (Jin et al., Proc. Natl. Acad. Sci. (USA), 88::6677 (1991)). A yeast membrane-associated FKBP-13 has also been identified, purified and partially sequenced; it binds both FK-506 and rapamycin, albeit with a substantially lower affinity than exhibited by FKBP-12, and in common with FKBP-12, possesses peptidylprolyl cis-trans isomerase (rotamase) activity (Nielsen et al., Proc. Natl. Acad. Sci. (USA), 89:7471 (1992)).

A 25 kDa high affinity rapamycin-binding protein has been identified and cloned from calf thymus, brain and spleen, and overexpressed in E. coli. This protein, which, like FKBP-12 and FKBP-13, exhibits peptidylprolyl cis-trans isomerase (rotamase) activity, shares identify with FKBP-12 (44%) and FKBP-13 (47%) in the C-terminal 97 amino acid region (Jin et al., J. Biol. Chem., 267: 10942 (1982); Galat et al., Biochemistry, 31:2427 (1992)).

Soldin et al. have purified to homogeneity and partially sequenced a low-abundance cytosolic immunophilin of a molecular mass of about 52 kDa. This protein has an unusually broad specificity in that it binds the cyclic undecapeptide cyclosporine, as well as the macrolides FK-506 and rapamycin, albeit at apparently different binding sites (Donnelly et al., Transplant. Proc., 23:2886 (1991); Soldin, U.S. patent application Ser. No. 07/782,761). This protein is devoid of rotamase activity, but inhibits cyclic AMP-activated protein kinase activity.

Characterizing immunophilins is important, not only for the elucidation of the mechanism of immunosuppressive action of FK-506 and rapamycin, but also because such proteins are valuable in developing quantitative binding assays for the circulating concentration of these drugs and their biologically active metabolites and derivatives, and in developing affinity systems for the isolation of immunosuppressive drugs from natural sources.

We have discovered, purified to homogeneity, and partially sequenced a novel cytosolic immunophilin that specifically binds FK-506 and rapamycin, but not cyclosporine A. This discovery is described below.

SUMMARY OF THE INVENTION

We have identified and purified to homogeneity from thymic lymphocytes a novel cytoplasmic immunophilin that specifically binds the immunosuppressant drugs FK-506 and rapamycin, but not cyclosporine. The novel immunophilin will also bind compounds chemically related to FK-506 and rapamycin, including metabolites, analogues or derivatives thereof. Although present in relatively small amounts, this immunophilin is ubiquitous and is present in a variety of normal and transformed human and animal cells, particularly in lymphoid tissues.

The novel immunophilin has an apparent molecular mass of about 14 kDa as determined by gel filtration and SDS-PAGE, and a minimum molecular mass calculated from the amino acid composition of about 14.6 kDa. Partial N-terminal sequence analysis of the 14.6 kDa protein shows no amino acid sequence homology to FKBP- 12 or to the membrane-associated FKBP-13.

In accordance with this invention, there is provided a homogeneous cytosolic immunophilin protein having a specific binding activity for FK-506 and rapamycin.

Further characteristics of this immunophilin are that it: exhibits no specific binding affinity for cyclosporin A (CsA); has a molecular mass of about 14.6 kDa; a Kd value of about 1.77 nM for a single high affinity [$^3$H]-FK-506 binding site; a $B_{max}$ for FK-506 of about 67 nmoles/mg protein; a pI of 6.5–7.5, in contrast to a pI of 8.8 for FKBP-12; an amino acid composition different than that of FKBP-12; a mole % excess of SER and THR compared to the GENBANK database average; has the N-terminal amino acid sequence (partially sequenced): NH$_2$-Lys-Leu-Pro-Tyr-Glu-Leu-Lys-Xaa-Asn-Val-Lys-Ala-Phe-Xaa-Xaa-Lys-Val- (wherein Xaa is yet undefined); and contains the additional internal amino acid sequences: -Val-Leu-Asp-Thr-Ala-Tyr-Glu-Tyr-Gly-Ala-Glu-Ala-Leu-Glu-, -Glu-Phe-Thr-Pro-Val-Phe-Gln-Ala-Xaa-Phe-, and -Ser-Leu-Val-Pro-Leu-Val-Gly-Xaa-Lys.

In one aspect, there is disclosed a purified complex between a biologically useful ligand and the 14.6 kDa protein, wherein said ligand possesses a specific binding affinity for the protein. The ligand can be an immunosuppressant, e.g., FK-506 or rapamycin-type macrolides, or an antibody to the protein.

In another aspect, there is described a polyclonal or monoclonal antibody to the 14.6 kDa immunophilin.

In a further aspect there is provided the 14.6 kDa immunophilin or an antibody thereto immobilized on a solid support.

In another aspect, there is provided a binding assay for determining the presence or quantity of a biologically useful ligand, e.g., FK-506, rapamycin and biologically-active metabolites, analogues or derivatives thereof, in a sample, e.g., a body fluid of a patient on immunosuppressant drug therapy, which comprises contacting said sample with the 14.6 kDa protein, wherein said protein preferably can be immobilized.

In yet another aspect, there is disclosed a method for purifying a biologically useful ligand wherein said ligand is present in a sample comprising a fermentation broth, a biological fluid such as human blood, or is a chemical entity that is a potential drug, and wherein said ligand is preferably an immunosuppressant, e.g., FK-506 or rapamycin, or is an antibody to the 14.6 kDa protein.

These and other aspects will become apparent by reference to the specification and appended claims.

BRIEF DESCRIPTION OF THE FIGURES

FIG. 4A shows a saturation curve, and FIG. 4B a Scatchard plot, of the binding of [$^3$H]-dihydro FK-506 to purified 14.6 kDa protein. In FIG. 4A, the curve marked with the filled circles represents specific binding, and the curved marked with filled squares represents nonspecific binding.

FIGS. 6A and 6B show a computer-produced graphical comparison of the amino acid composition of the FKBP-14.6 and FKBP-12 immunophilins. FIG. 6A represents the 14.6 kDa protein and FIG. 6B represents the 12 kDa protein.

DESCRIPTION OF THE INVENTION AND PREFERRED EMBODIMENTS

We have demonstrated the presence in calf thymus T-lymphocytes of a low molecular weight (14.6 kDa) cytosolic immunophilin protein (hereinafter "FKBP- 14.6") that exhibits high affinity specific binding to the immunosuppressant agents FK-506 and rapamycin, but does not bind cyclosporine. The protein is distinct from calf thymus FKBP-12 and membrane-associated human FKBP-13 by a number of physicochemical criteria, including molecular weight, amino acid composition, partial N-terminal and intermolecular amino acid sequences, and isoelectric pH (i.e., pI), as will be detailed below in the Examples.

The FKBP-14.6 protein, as such or immobilized on a solid support, can be used for a variety of purposes, including diagnostic, purification or investigatory procedures. Affinity matrices may be constructed as described in U.S. Pat. Nos. 5,047,512 and 5,109,112 between FKBP-14.6 and an immobilizing matrix such as Sepharose (Pharmacia) by conventional CNBr activation techniques, using standard spacer arms (Pierce Chem. Co., Rockford, Ill., 1989 Handbook and General Catalog, pp. 283–312). Free or immobilized on a solid support, FKBP-14.6 may be used as a specific binding partner in conventional quantitative binding assay methods for determining the concentration in samples of FK-506 and rapamycin, as well as compounds chemically related thereto, including their biologically active metabolites, derivatives and analogues (Donnelly et al., *Transplant. Proc.*, 23:2886 (1991)). Immobilized FKBP-14.6 can be used as described in Siekierka et al., U.S. Pat. No. 5,047,512 as a binding matrix for the research or bulk isolation from soil samples or fermentation broths of chemical compounds chemically related to FK-506 and/or rapamycin with pharmaceutical potential. The above-described immobilized affinity matrix can be prepared that reversibly binds such compounds in a complex, from which the compound can be eluted with aqueous buffer reagents of increasing ionic strengths. The above-described matrices are also useful in screening candidate compounds that, like FK 506 or rapamycin, can have immunosuppressive activity and, therefore, are useful in developing other classes of immunosuppressive drugs.

The purified 14.6 kDa protein may be used as the immunogen in raising polyclonal antibodies and monoclonal antibodies directed to specific epitopes by conventional methods (see, e.g., Harlow et al., *Antibodies, A Laboratory Manual*, Cold Spring Harbor Press, Cold Spring Harbor, N.Y., 1988). As FKBP-14.6 has been purified to homogeneity, oligonucleotide probes can be used to identify the gene for this protein, thereby allowing it to be produced by known recombinant DNA techniques.

For use in binding studies, native FK-506 may be isolated from fermentation broths (U.S. Pat. No. 5,109,112) or obtained from Fujisawa Pharmaceutical Co., Osaka, Japan. Rapamycin and [$^3$H]-rapamycin were obtained from Wyeth-Ayerst Co., Princeton, N.J. [$^3$H]-dihydro FK-506 was prepared by exposing native FK-506 to tritium gas in the presence of the reducing agent TRIS (triphenyl-phosphine)rhodium I chloride, followed by purification by normal and reverse phase chromatographies (Amersham Corp., Arlington Heights, Ill.). [$^3$H]-dihydro FK-506 was 98+% pure as determined by TLC, and had a specific activity of 51 Ci/mmol or 63.2 mCi/mg.

EXAMPLE 1

Purification of the FKBP-14.6 Binding Protein

The initial steps in the purification of the 14.6 kDa protein from calf thymus were similar to those previously described for isolating immunophilins from a human JURKAT T-lymphocyte cell line (Palaszynski et al., *Clin. Biochem.*, 24:63 (1991), which is incorporated herein by reference). Briefly, calf thymus (Pel-Freeze, Rogers, Ariz.) was cut into 1–2 cm pieces and homogenized in two steps in 5 mM potassium phosphate buffer, pH 6.8, containing 3 mM EDTA, 1.2 mM EGTA and 20 µM phenyl methyl sulfonyl fluoride at 4° C. Initial tissue disruption was done in a Waring Blender, followed by homogenization using a Polytron (Brinkman Instr., Westbury, N.Y.) at medium speed for 3–5 minutes. The supernatant fluid obtained after centrifuging the homogenate at 17,000×g for 30 minutes at 5° C. was filtered through cheese cloth to remove all debris and to defat it, and then centrifuged at 100,000×g for 60 mins. at 5° C. This final supernatant fluid ("cytosol") was preliminarily fractionated using Centricon microconcentrators Centriprep-30 and Centriprep-10 (Amicon Corp., Beverly, Mass.) to obtain 10–30 kDa protein fractions.

The pooled 10–30 kDa protein fractions were subjected to preparative free solution isoelectric focusing in a Rotofor cell (Bio-Rad Co., Richmond, Calif.). The pooled 10–30 kDa fractions (50 ml) were focused for 5–6 hours at a constant 12 W using a power supply with a maximum of 1200 volts. The initial voltage was 200–250 and the final voltage at the end of the run was 500–550. Samples between pH 6.5 and 7.5 were pooled and re-isofocused for 6 hours to improve the separation. After pooling the pH 6.5–7.5 fractions and concentrating the protein using Centricon micro concentrators, the protein solution was adjusted to 1M NaCl, incubated for 2–4 hours at 4° C., dialyzed overnight against two changes of 5 mM phosphate buffer, pH 6.8, to remove ampholyte, then filtered through a 8 kDa cut-off membrane to remove lower molecular weight contaminants. This step removes the bulk of the contaminating FKBP-12 (pI 8.8, Schreiber et al., WO 91/04321) and 17 kDa cyclophilin (pI 9.3, Handschumacher et al., U.S. Pat. No. 5,047,512).

Figure 1:
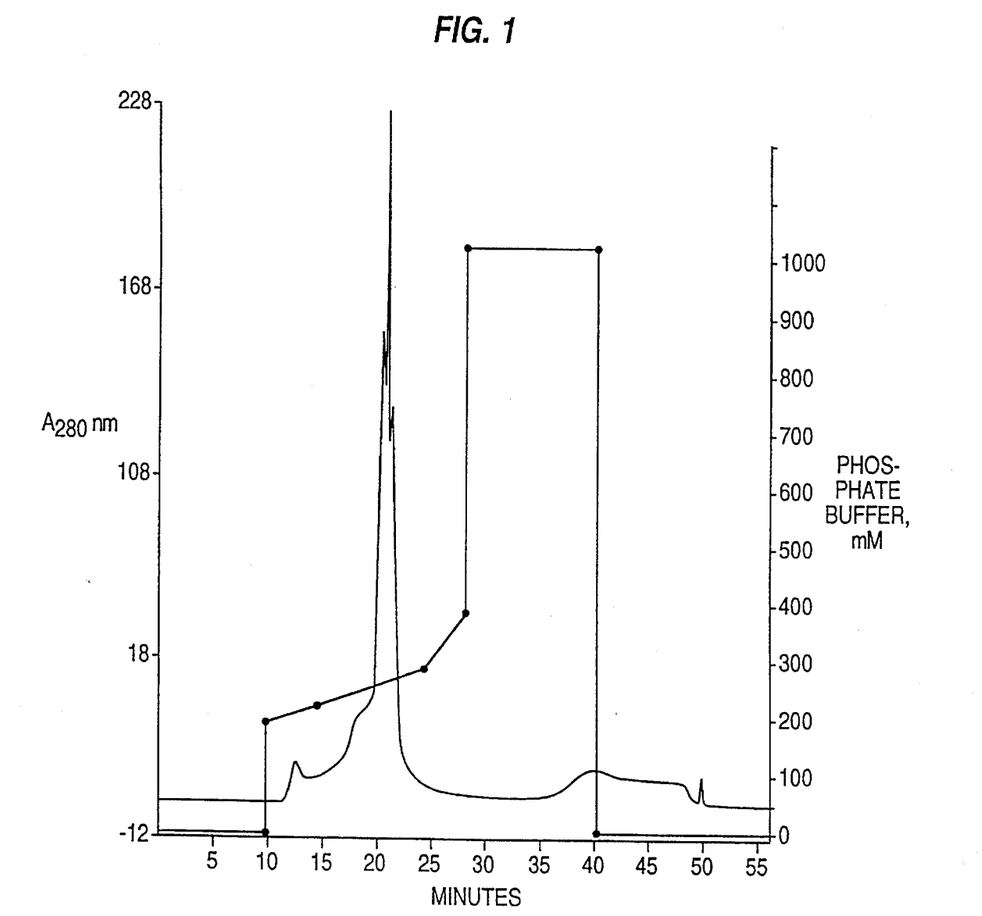
FIG. 1 shows the weak cation exchange chromatographic pattern of an isoelectric focused protein fraction. The curve connecting filled circles describes the phosphate buffer elution pattern. The solid curve represents the ultraviolet absorbencies at 280 nm of eluted protein fractions.

The purified focused protein (pI 6.5–7.5) from the previous step was fractionated on an HPLC gradient cation exchange column. A 0.5 ml sample of the focused protein was injected into a Beckman Industries, Inc. (Fullerton, Calif.) Spherogel TSK-CM 2SW, 4.6 mm×25 cm column, equilibrated with 5 mM phosphate buffer, pH 6.8, at a flow rate of 0.5 mL/min. Less than 1% of the protein applied bound to the column. An elution gradient of 5–1000 mM phosphate buffer over 60 mins. was applied. The effluent was monitored by its $A_{280nm}$ absorbency (-•-•- in FIG. 1). FKBP-14.6 eluted at about 200–250 mM phosphate buffer (20–30 mins.), as seen in the elution profile shown in FIG. 1. Fractions representing purified FKBP-14.6 were pooled and concentrated using Amicon Centricon cut-off filters.

Figure 2:
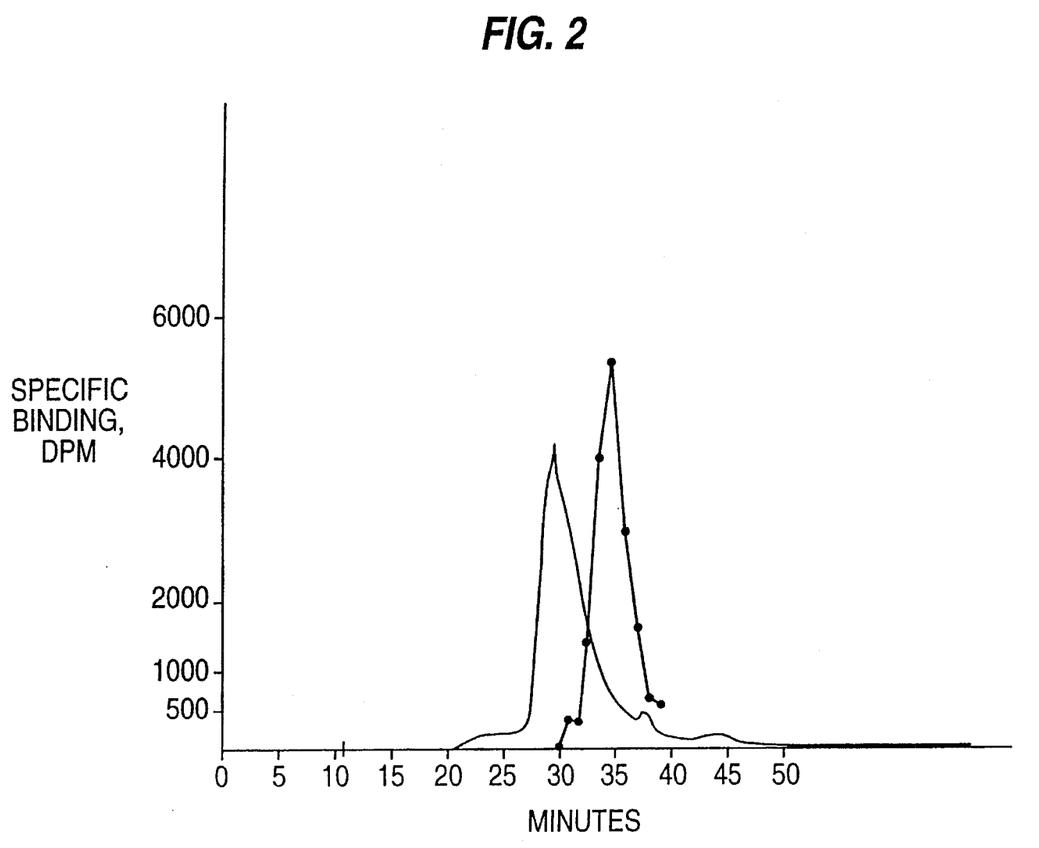
FIG. 2 shows the size exclusion chromatographic pattern of the protein fraction eluting from weak cation exchange chromatography and the binding pattern for [$^3$H]-dihydro FK-506. The curve connecting filled circles represents the elution pattern of the 14.6 kDa protein. The solid curve represents the elution pattern of a 14 kDa molecular mass standard.

The FKBP-14.6 pool isolated from the cation exchange column (2 mL) was further fractionated on a Bio-Rad BioSil-125 HPLC 7.5×600 mm gel filtration column operating at a flow rate of 0.6 mL/min. with 50 mM phosphate buffer - 100 mM NaCl. The purified 14.6 kDa protein eluted as a single peak (-•-•-) slightly behind a 14 kDa molecular mass standard (------) (FIG. 2).

Figure 3:
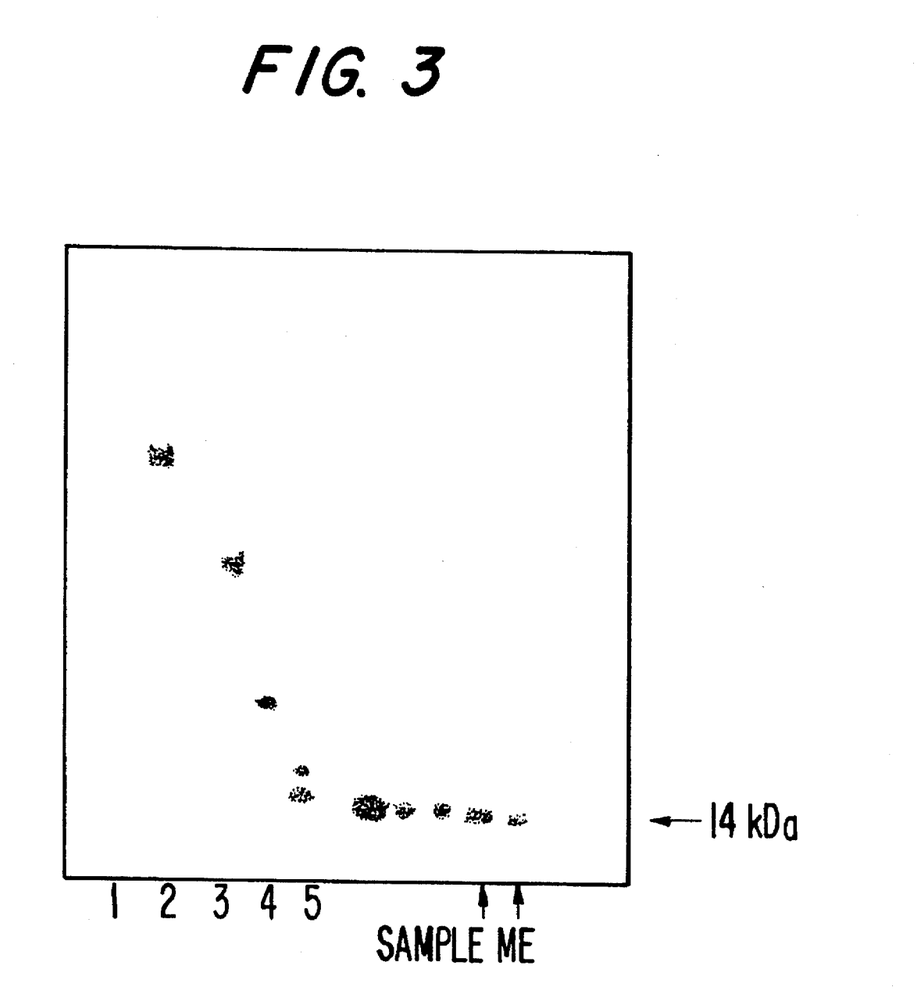
FIG. 3 shows the SDS-PAGE pattern of the purified 14.6 kDa immunophilin protein. Lane 1 is a BSA marker (68 kDa), lane 2 an alcohol dehydrogenase marker (39 kDa), lane 3 a triosephosphate isomerase marker (26.6 kDa), and lane 5 a lysozyme marker (14.3 kDa). The four lanes labeled "Sample" represent four different preparations of purified 14.6 kDa binding protein. The lane labeled "ME" represents a preparation of 14.6 kDa protein treated with 62 -mercaptoethanol.

The protein eluted from the gel filtration column was analyzed for homogeneity using 15% SDS-PAGE±mercaptoethanol according to Laemmli, Nature, 227:680 (1970), and visualized using DAIICHI silver staining (Ohsawa et al., Anal. Biochem., 135:409 (1983)). Protein estimation was performed according to the Lowry method (Peterson, Anal. Biochem., 83:346 (1977)). A single band corresponding to a molecular mass of about 14 kDa was observed (FIG. 3). In this figure, lane 1 is a BSA marker (68 kDa), lane 2 an alcohol dehydrogenase marker (39 kDa), lane 3 a triosephosphate isomerase marker (26.6 kDa), lane 4 a trypsin inhibitor marker (20.1 kDa), and lane 5 a lysozyme marker (14.3 kDa). Four preparations of purified 14 kDa binding protein are shown in the lanes labeled "sample". the use of mercaptoethanol (lane ME) showed that the purified 14 kDa contained no apparent subunits.

For assessing the degree of purification, competition between tracer amounts of labeled FK-506 and unlabeled FK-506 was measured at various stages of the purification, as described below.

A summary of the purification data is shown in Table 1.

TABLE 1

| Summary of Purification | | | | |
|---|---|---|---|---|
| Step | Protein (mg/ML) | Specific binding (DPM/mg) | Recovery % | Fold Purification |
| Isoelectric focusing | 5.08 | $2.4 \times 10^4$ | 100 | — |
| Cation exchange | 0.608 | $4.0 \times 10^4$ | 12 | 1.66 |
| Size exclusion | 0.022 | $5.3 \times 10^5$ | 0.43 | 22 |

EXAMPLE 2

Binding Assay For FK-506 and Rapamycin

Binding of [$^3$H]-dihydro FK-506 to protein fractions was assessed using the LH-20 assay as described by Handschumacher et al., Science, 226:544 (1984). Briefly, in a final volume of 250 µl, labeled FK-506 (2–5.35 nM in EtOH) and 2–5 µg protein (200 µl) were preliminarily incubated, and the competition reaction begun by the addition of varying concentrations of unlabeled FK-506 or rapamycin. Following 20 minutes at room temperature, a 200 µl aliquot of the reaction mixture was filtered through a 1.8 mL bed-volume Sephadex LH-20 column equilibrated with 20 mM Tris buffer, pH 7.2, containing 5 mM 2-mercaptoethanol and 0.05 % NAN$_3$. Elution with five 250 µL portions of the assay buffer separated protein-bound [$^3$H]-dihydro FK-506 from free labeled drug (Sjovall et al., in Giddlings et al., Advances in Chromatography, Marcel Dekker, Inc., N.Y., vol. 6, pp. 119–170 (1968)). Radioactivity in the 1.25 mL eluate was measured by liquid scintillation spectrometry (Optima Gold Scintillation cocktail, Packard Chemicals, Meriden, Conn.) operating at 59% efficiency. Non-specific binding was estimated by the addition of 1 µM unlabeled FK-506, which displaced ≧95% of the bound radioligand from binding sites.

EXAMPLE 3

Scatchard and Hill Plot Calculations

Figure 4A:
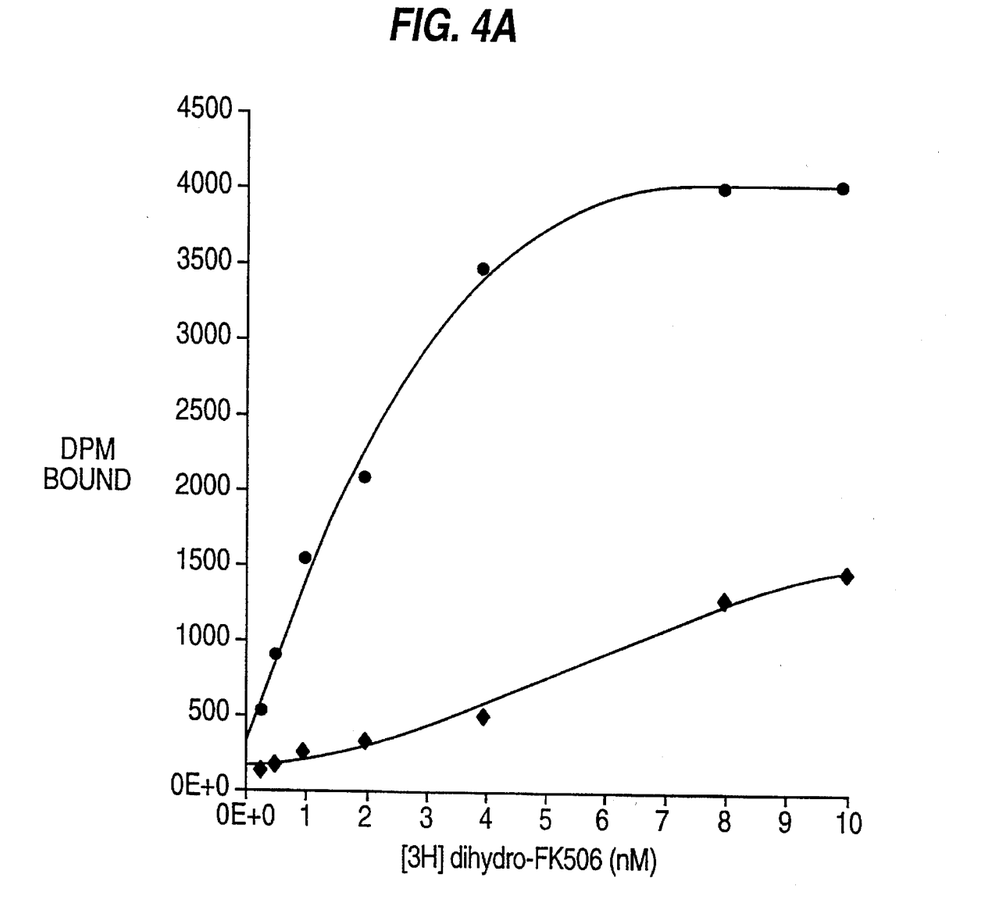
Figure 4B:
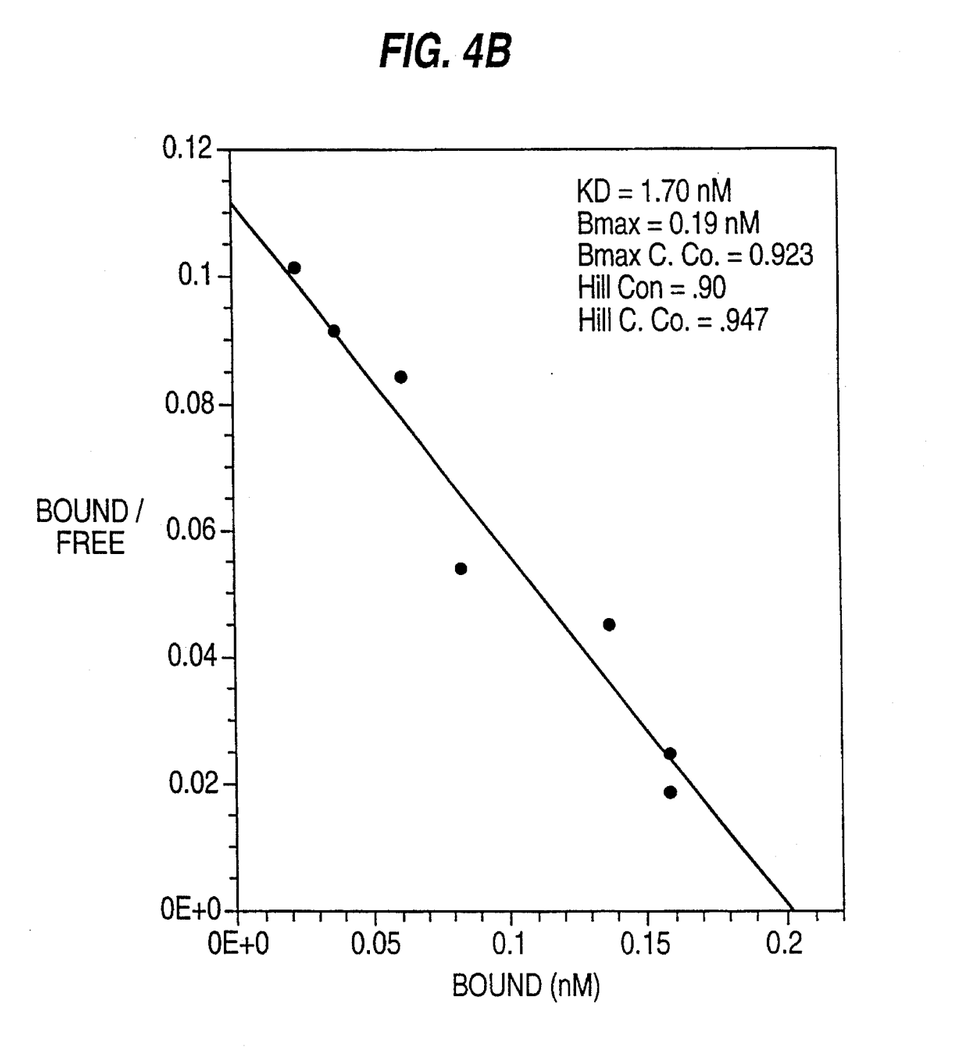

To obtain binding site information for the FKBP- 14.6 protein, Scatchard plots were obtained in saturation experiments using eight concentrations of labeled FK-506 (0.25–12 nM) in triplicate (FIG. 4A). In FIG. 4A, specific binding is shown by (-•-•-) and non-specific binding by (-♦-♦-). Data were analyzed with the EBDA and Ligand Corporation programs. Scatchard plot data (B/F v. B, FIG. 4B) revealed linear binding, and Hill coefficients of near unity, suggesting that only a single class of binding sites was present. Analysis gave a Kd value of 1.77 nM with a binding site B$_{max}$ of about 0.67 nmoles/mg protein.

EXAMPLE 4

Determination of Binding Site Homologies and Affinities

Figure 5:
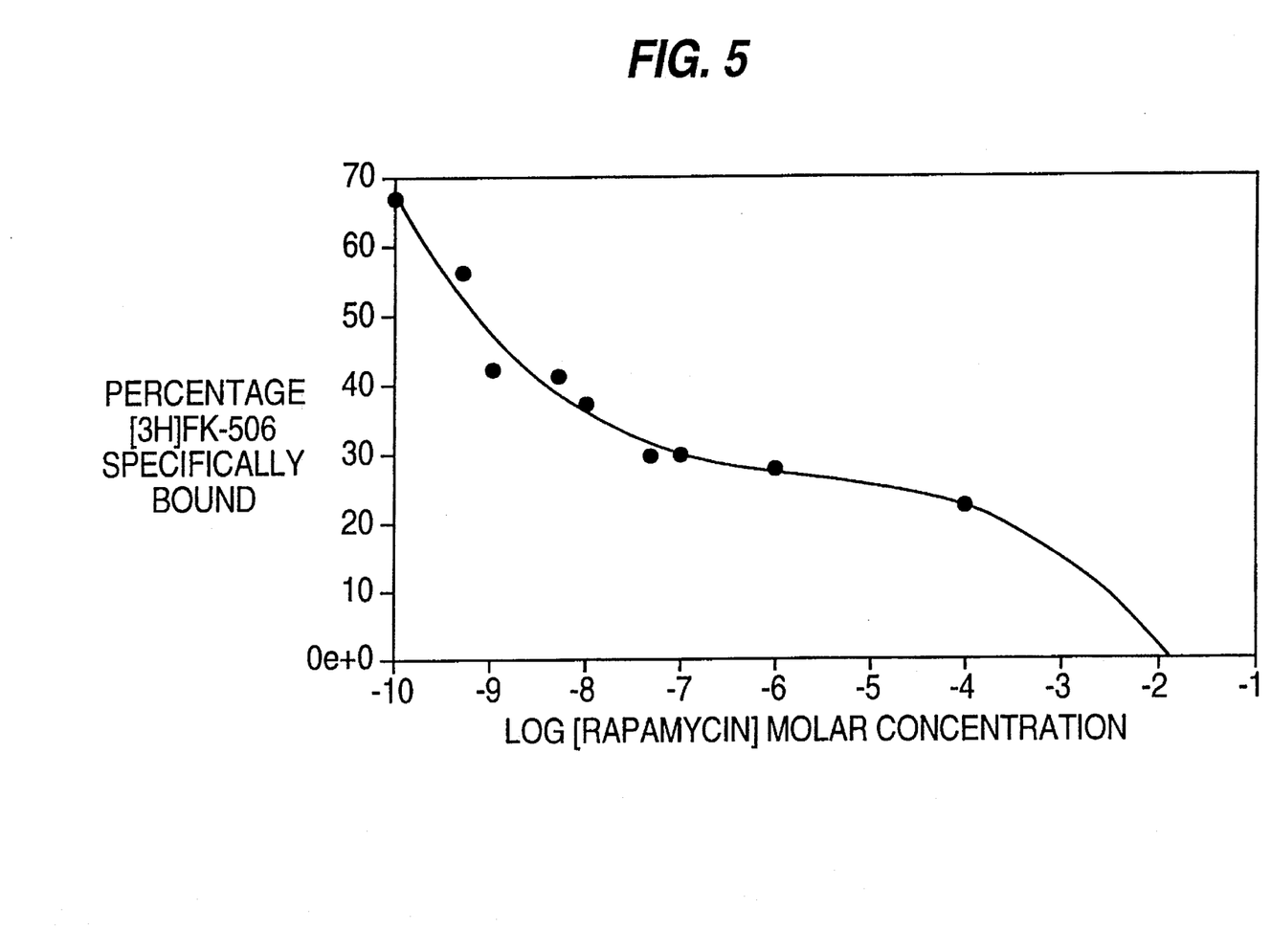
FIG. 5 shows binding competition between [$^3$H]-dihydro FK-506 and unlabeled rapamycin for binding to the purified 14.6 kDa protein.

To determine if rapamycin interacted with FK-506's binding site on FKBP-14.6, competition studies were carried out using 6 nM [$^3$H]-dihydro FK-506 and 8 concentrations of rapamycin (0.1 nM-1 μM) in a buffer containing 0.2% Tween-20. Unlabeled FK-506 (1 μM) was used to define nonspecific binding. Rapamycin displaced [$^3$H]-dihydro FK-506 in a statistically significant (P<0.007) biphasic manner (FIG. 5). The Kd values for the high and low affinity binding sites were 23 pM and 226 nM, respectively, at a 50% receptor occupation of both high and low affinity sites. We could not detect specific binding of [$^3$H]-CsA to FKBP-14 using the LH-20 assay.

EXAMPLE 5

Amino Acid Composition of FKBP-14.6 and FKBP-12

The total amino acid composition of the FKBP-14.6 immunophilin was determined in duplicate by conventional methods. Averaged mole % data are shown in Table 2, and are compared with counterpart data for a sample of bovine thymus FKBP-12.

TABLE 2

Amino Acid Composition of FKBP-14.6 and FKBP-12

| Amino Acid | Mole % FKBP-14.6 | Mole % FKBP-12 |
|---|---|---|
| Ala | 7.8 | 4.7 |
| Gln | 6.6 | 4.7 |
| Ile | 4.3 | 5.6 |
| Phe | 5.1 | 4.7 |
| Cys | * | 0.9 |
| Arg | 4.8 | 5.6 |
| Glu | * | 6.5 |
| Leu | 10.5 | 6.5 |
| Pro | 3.1 | 6.5 |
| Trp | * | 0.9 |
| Asn | 7.7 | 1.9 |
| Gly | 8.9 | 12.1 |
| Lys | 2.9 | 7.5 |
| Ser | 12.6 | 4.7 |
| Tyr | 3.3 | 2.8 |
| Asp | * | 5.6 |
| His | 2.0 | 1.9 |
| Met | 2.3 | 1.9 |
| Thr | 8.6 | 6.5 |
| Val | 9.4 | 8.4 |

*Not available.

The calculated minimum molecular weight for FKBP-14.6 was 14,592, and for FKBP-12, 11,765.

Figure 6A:
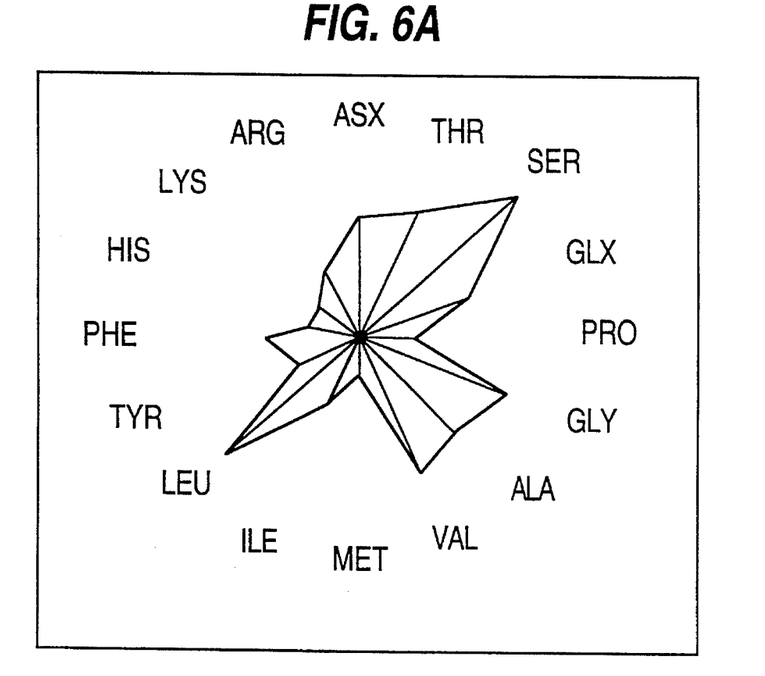
Figure 6B:
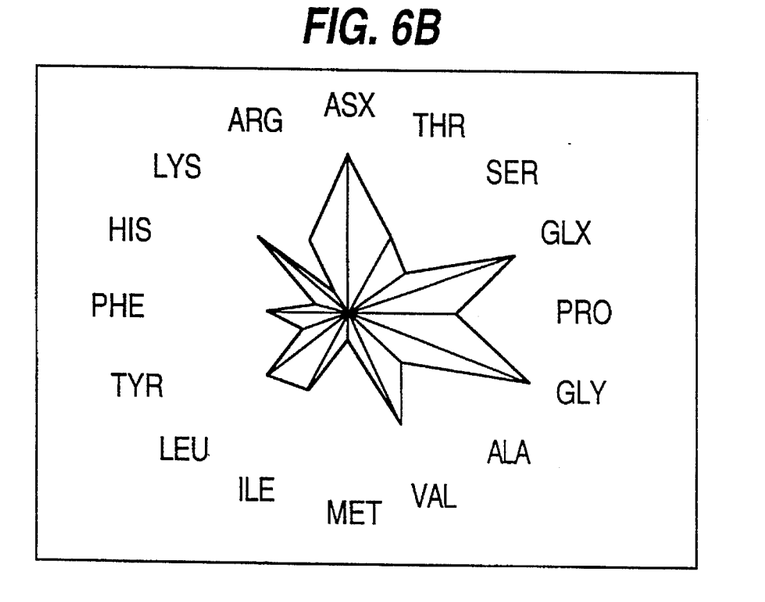

FIGS. 6A and 6B compare the mole % amino acid composition of the FKBP-14.6 protein of the invention and FKBP-12, respectively, graphically. The circle diagrams show the mole % of each amino acid as a vector from the center of a circle, with the magnitude of the vector being equal to the mole % of the amino acid. Circle plots were generated using the AAPROP and AAFIG computer programs of Shaw, Bio/Techniques, 12(6), 886 (1992). It is clear that the two proteins have widely dissimilar compositions.

Figure 7:
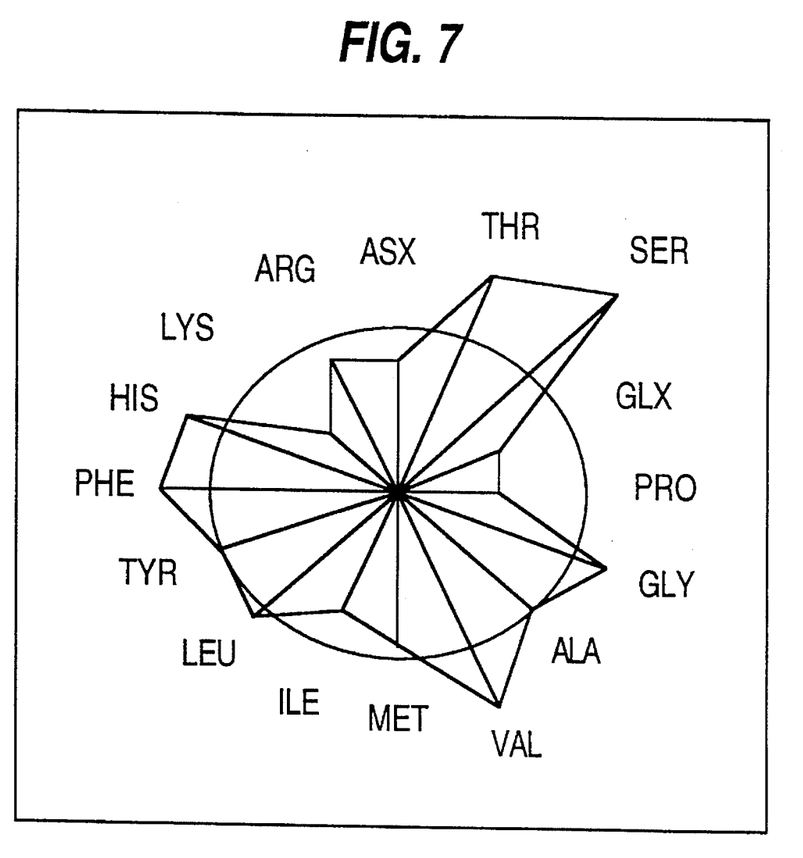
FIG. 7 is a circle plot of the amino acid composition of purified 14.6 kDa binding protein in comparison with the average of all known proteins in the Genbank database.

FIG. 7 is a similar circle plot of the FKBP-14.6 immunophilin of the invention as compared to the average compositions of all proteins in the Genbank database (the circle represents the database average). FKBP-14.6 is substantially elevated in Thr and Ser as compared to the average protein and slightly deficient in Lys, Pro and Gln.

EXAMPLE 6

Amino Acid Sequences of FKBP-14.6

The partial N-terminal amino acid sequences of FKBP-14.6 were determined by automated Edman degradation of the intact molecule. The binding protein was transferred to PVDF membranes by the procedure of Matsudaira et al., J. Biol. Chem., 261:10035 (1987), and membrane pieces were loaded into the cartridge of a gas phase sequencer. Overlapping fragments were generated by proteolytic (tryptic) digest and chemical cleavage. The resulting peptides were resolved by rpHPLC with absorbency being monitored at 214 nm and 280 nm. Various peaks were loaded to a Porton peptide disk and sequenced conventionally to obtain internal sequences. A homology search for the N-terminal amino acid sequence obtained showed that this sequence could not be attributed to any known sequence. In Table 3 are shown the amino acid sequences of the N-terminal (Seq. ID No. 1) and internal sequences; Seq. ID No. 2, fragment no. 112; Seq. ID No. 3, fragment no. 121; and Seq. ID No. 4, fragment no. 111. For comparison, the N-terminal sequences of FKBP-12 (Seq. ID No. 5, U.S. Pat. No. 5,109,112), and membrane-associated FKBP-13 (Seq. No. 6, Jin et al., 1991, above) are shown.

TABLE 3

Amino Acid Sequences of FKBP-14.6 Immunophilin (Seq. Nos. 1-4)

| Seq. No. | 1 | 2 | 3 | 4 | 5 | 6 | 7 | 8 | 9 | 10 | 11 | 12 | 13 | 14 | 15 | 16 | 17 |
|---|---|---|---|---|---|---|---|---|---|---|---|---|---|---|---|---|---|
| 1. | NH$_2$—Lys— | Leu— | Pro— | | | Tyr— | Glu— | Leu— | Lys— | Xaa— | Asn— | Val— | Lys— | Ala— | Phe—Xaa—Xaa—Lys— | | Val— |
| 2. | | —Val— | Leu— | Asp— | Thr— | Ala— | Tyr— | | | Glu— | Tyr— | Gly— | Ala— | Glu— | Ala—Leu—Glu— | | |
| 3. | | —Glu— | Phe— | Thr— | | Pro— | Val— | Phe— | | Gln— | Ala— | Xaa— | Phe— | | | | |
| 4. | | —Ser— | Leu— | Val— | | Pro— | Leu— | Val— | | Gly— | Xaa— | Lys | | | | | |
| 5. | NH$_2$—Gly— | Val— | Gln— | | | Val—Phe—Thr— | | | Ile— | Ser— | Pro— | Gly— | Asp— | Gly— | Asn—Thr—Phe— | Pro— | Lys— |
| 6. | NH$_2$—Thr— | Gly— | Ala— | | | Glu—Gly—Lys— | | | Arg— | Lys— | Leu— | Gln— | Ile— | Gly— | Val— | Lys—Lys— | Arg—Val— |

As the novel FKBP-14.6 kDa immunophilin has been purified to homogeneity and partially sequenced, oligonucleotide probes can be constructed and used to identify the gene, thereby allowing the protein to be produced by art-recognized recombinant DNA techniques. For cloning purposes, oligomers may preferably be made to amino acids 1–7 for the N-terminal sequence, amino acids 1–13 for the #112 tryptic fragment, amino acids 1–8 for the 121 fragment, and amino acids 1–7 for the #111 fragment.

What is claimed is:

1. A method for, quantifying in a sample one or more analytes contained therein selected from the group consisting of FK-506, rapamycin and a compound chemically related to FK-506 or rapamycin, comprising the steps of:
  (a) contacting said sample with an isolated and purified, substantially homogeneous cytosolic immunophilin protein preparation comprising a binding protein having: specific affinity for FK-506, rapamycin and chemically related compounds, but not for cyclosporine; a molecular mass in the range of about 14–15 kDa by SDS-PAGE: a partial N-terminal amino acid sequence: NH$_2$-Lys-Leu-pro-Tyr-Glu-Leu-Lys-Xaa-Asn-Val-Lys-Ala-Phe-Xaa-Xaa-Lys-Val- (SEQ ID NO. 1), wherein Xaa has not been determined; and, an isoelectric pH of about 6.5–7.5, under conditions such that complex formation occurs between said binding protein and said analyte, if said analyte is present,
  (b) quantifying the amount of said formed complex; and
  (c) correlating the amount of said complex with the quantity of said analyte in said sample.

2. A method as claimed in claim 1, wherein said binding protein is of animal origin.

3. A method as claimed in claim 1, wherein said binding protein is of human origin.

4. A method as claimed in claim 1, wherein said binding protein further comprises a protein having a partial internal amino acid sequence: Val-Leu-Asp-Thr-Ala-Tyr-Glu-Tyr-Gly-Ala-Glu-Ala-Leu-Glu (SEQ ID NO. 2).

5. A method as claimed in claim 1, wherein said binding protein further comprises a protein having a partial internal amino acid sequence: Glu-Phe-Thr-Pro-Val-Phe-Gln-Ala-Xaa-Phe (SEQ ID NO. 3), where Xaa has not been determined.

6. A method as claimed in claim 1, wherein said binding protein further comprises a protein having a partial internal amino acid sequence: Ser-Leu-Val-Pro-Leu-Val-Gly-Xaa-Lys (SEQ ID NO. 4), where Xaa has not been determined.

7. A method as claimed in claim 1, wherein said binding protein is immobilized on a solid support.

8. A method as claimed in claim 1, wherein said binding protein is in free solution during said complex formation with said analyte.

9. A method for isolating from a sample a compound capable of binding to the immunophilin of claim 1 or an antibody directed to said immunophilin, comprising the steps of:

(a) preparing an affinity matrix comprising said immunophilin immobilized on a solid support;

(b) contacting said sample with said affinity matrix under conditions such that said compound or antibody binds to said immobilized immunophilin to form a binding complex;

(c) dissociating said compound or antibody from said binding complex; and, (d) collecting said dissociated compound or antibody.

10. A method of claim 9, wherein said compound is FK-506, rapamycin or a chemically related compound.

11. A method of detecting in a sample FK-506, rapamycin or a chemically related compound, comprising the steps of:

(a) contacting said sample with the binding protein of claim 1 under conditions such that complex formation occurs between said protein and said FK-506, rapamycin or chemically related compound; and (b) detecting said complex.

* * * * *